US005780015A

United States Patent [19]
Fisher et al.

[11] Patent Number: 5,780,015
[45] Date of Patent: Jul. 14, 1998

[54] DENTIFRICE FOR THE TREATMENT OF DENTINAL HYPERSENSITIVITY HAVING LIMITED ASTRINGENCY

[75] Inventors: Steven W. Fisher, Middlesex; Edward A. Tavss, Kendall Park; Marilou T. Joziak, South River; Robert J. Gambogi, Belle Mead, all of N.J.

[73] Assignee: Colgate Palmolive Company, New York, N.Y.

[21] Appl. No.: 856,265

[22] Filed: May 14, 1997

[51] Int. Cl.⁶ ................... A61K 7/16; A61K 7/18
[52] U.S. Cl. ......................... 424/52; 424/49
[58] Field of Search ............................ 424/49–58

[56] References Cited

U.S. PATENT DOCUMENTS

| | | | |
|---|---|---|---|
| 4,689,214 | 8/1987 | Niles et al. | 424/49 |
| 4,765,984 | 8/1988 | Vellekoop et al. | 424/49 |
| 4,814,163 | 3/1989 | Barth | 424/49 |
| 4,828,822 | 5/1989 | Muhlemann et al. | 424/52 |
| 4,945,087 | 7/1990 | Talwar et al. | 424/49 |
| 4,992,276 | 2/1991 | Dills et al. | 424/49 |
| 5,071,638 | 12/1991 | Yoshie et al. | 424/49 |
| 5,100,650 | 3/1992 | Calin et al. | 424/49 |
| 5,298,238 | 3/1994 | Hussein et al. | 424/49 |
| 5,407,664 | 4/1995 | Konopa | 424/49 |
| 5,534,243 | 7/1996 | Dixon et al. | 424/49 |
| 5,690,911 | 11/1997 | Mirajkar et al. | 424/49 |
| 5,693,314 | 12/1997 | Campbell et al. | 424/49 |

*Primary Examiner*—Shep K. Rose
*Attorney, Agent, or Firm*—Paul Shapiro

[57] ABSTRACT

A two component desensitizing dentifrice composition is disclosed which comprises a first dentifrice component containing a desensitizing potassium salt such as potassium nitrate and a second dentifrice component containing a stannous salt desensitizing agent such as SnF2, the first and second dentifrice components being maintained separate form the other until dispensed for application to teeth requiring relief from dentine hypersensitivity, at least one of the dentifrice components containing the oxyethylated reaction product of hydrogenated castor oil to reduce astringency when the combined product is used by consumers.

10 Claims, No Drawings

DENTIFRICE FOR THE TREATMENT OF DENTINAL HYPERSENSITIVITY HAVING LIMITED ASTRINGENCY

BACKGROUND OF THE INVENTION

1. Field of the Invention

The present invention relates to a desensitizing dentifrice composition containing potassium and stannous salts to reduce the discomfort and pain associated with dental hypersensitivity and more particularly to a two-component desensitizing dental composition containing stannous and potassium salts having limited astringency.

2. The Prior Art

Dentinal hypersensitivity is defined as acute, localized tooth pain in response to physical stimulation of the dentine surface as by thermal (hot or cold) osmotic, tactile combination of thermal, osmotic and tactile stimulation of the exposed dentin. Exposure of the dentine, which is generally due to recession of the gums, or loss of enamel, frequently leads to hypersensitivity.

Stannous salts such as $SnF_2$ have been indicated clinically to be efficacious in the reduction of dentinal hypersensitivity. It is also known to the art that potassium salts are effective in the treatment of dentinal hypersensitivity. For example, U.S. Pat. No. 3,863,006 discloses that potassium salts such as potassium nitrate when incorporated in toothpastes desensitize the teeth.

In copending patent application Ser. No. 08/594,605 filed Feb. 2, 1996, now U.S. Pat. No. 5,693,314 there is disclosed a dental desensitizing composition which includes a first dentifrice component containing a desensitizing potassium salt such as potassium nitrate and a second dentifrice component containing a stannous salt desensitizing agent are housed in a container wherein the dentifrice components are maintained separate from each other and are not admixed until simultaneous application to the teeth is to be performed.

Although the simultaneous application of the stannous and potassium salt containing dentifrices are effective in the treatment of dentinal hypersensitivity, the stannous and potassium salt present in the dentifrices impart an astringent, bitter, sour taste when the dentifrice is used which reduces the acceptability of the dentifrice by consumers requiring treatment of dentinal hypersensitivity. Therefore, there is a need for a means whereby the astringency of dentifrices containing stannous and potassium salts can be ameliorated so that such dentifrices will be more acceptable for use by consumers.

SUMMARY OF THE INVENTION

In accordance with the present invention there is provided a dentifrice composition for the treatment of dentinal hypersensitivity having limited astringency, the composition being comprised of separate dentifrice components containing either a stannous salt or a potassium salt where the astringency of the components is limited by the presence therein of at least about 6% by weight of an oxyethylated hydrogenated castor oil.

As will hereinafter be demonstrated, the presence of the oxyethylated hydrogenated castor oil in the dentifrice components provides a product of substantially reduced astringency having improved palatability when used by the consumer.

DESCRIPTION OF THE PREFERRED EMBODIMENTS

Oxyethylated hydrogenated castor oil is a known composition and is prepared by reacting for example about 40 to about 60 moles of ethylene oxide with one mole of hydrogenated castor oil. These compositions are sold commercially under the trademark Cremophor available from Badische Anilin-und Sodafabrick, Federal Republic of Germany.

Oxyethylated hydrogen castor oil has been used as an emulsifier in oral care products containing stannous salts. For example, U.S. Pat. No. 4,828,822 discloses the use of the Cremophor RH, identified as an ester of hydrogenated castor oil fatty acids with oxyethylated glycerol at concentration of 0.1% by weight as an emulsifier in a mouth rinse containing stannous fluoride.

In the present invention, the oxyethylated hydrogenated castor oil to be effective to reduce astringency is incorporated into a dentifrice component containing the stannous or potassium salt at a concentration of at least about 6% by weight and preferably about 6 to about 8% by weight. Amounts greater than about 8% by weight of the oxyethylated hydrogenated castor oil are to be avoided as such amounts impair the rheology of the dentifrice rendering the product unacceptable for use by consumers.

As will hereinafter be demonstrated at concentrations below about 6% by weight, the oxyethylated hydrogenated castor oil has limited effect on reducing astringency experienced by consumers.

Polyoxyethylene hydrogenated castor oil is disclosed in European Patent 251 542 as being effective in reducing the astringency derived from zinc salts in dentifrice products when the polyoxyethylene hydrogenated castor oil in incorporated in the dentifrice composition at a concentration of 0.1 to 5% by weight and preferably 0.3 to 4% by weight. The European Patent further teaches that when the amount of polyoxyethylene hydrogenated castor oil is present in the dentifrice composition at levels greater than 5%, an undesirable oiliness is imparted by the polyoxyethylene hydrogenated castor oil.

In the practice of the present invention, the source of desensitizing potassium ion is generally a water soluble potassium salt including potassium nitrate, potassium citrate, potassium chloride, potassium bicarbonate and potassium oxalate, potassium nitrate being preferred. The potassium salt is generally incorporated in the compositions of the present invention at a concentration of about 8 to about 12% by weight and preferably about 3 to about 10% by weight.

To prepare the potassium salt desensitizing dentifrice component of the present invention, the potassium salt ingredient is incorporated in a dentifrice which includes a vehicle which contains water, humectant, surfactant and a polishing agent.

The humectant is generally a mixture of humectants, such as glycerol, sorbitol and polyethylene glycol of molecular weight in the range of 200–1000, but other mixtures of humectants and single humectants may also be employed. The humectant content is in the range about of 10% to about 80% by weight and preferably about 40 to about 50% by weight. The water content is in the range of about 10 to about 20% by weight.

Inorganic thickeners may be included in the dentifrice component in which potassium salts are included as an ingredient include fumed silicas such as Cabosil available from Cabot Corporation, and thickening silicas including those available from Crosfield Chemicals designated Sorbosil TC-15 or Sylox 15 from W. R. Grace.

Organic thickeners of natural and synthetic gums may also be incorporated in the dentifrice component of the present invention in which a potassium salt is an ingredient. Examples of such thickeners are carrageenan (Irish moss), xanthan gum, sodium carboxymethyl cellulose, starch, polyvinylpyrrolidone, hydroxyethylpropylcellulose, hydroxybutyl methyl cellulose, hydroxypropyl methyl cellulose, and hydroxyethyl cellulose. The organic thickener may be incorporated in the compositions of the present invention at a concentration of about 0.1 to about 3% by weight and preferably about 0.5 to about 1% by weight.

Surface active agents may be incorporated in the dentifrices in which a desensitizing potassium salt is included as an ingredient to provide foaming properties. The surface-active material is preferably anionic, suitable examples of which include higher alkyl sulfates such as potassium or sodium lauryl sulfate which is preferred, higher fatty acid monoglyceride monosulfates, such as the salt of the mono-sulfated monoglyceride of hydrogenated coconut oil fatty acids, alkyl aryl sulfonates such as sodium dodecyl benzene sulfonate, higher fatty sulfoacetates, higher fatty acid esters of 1,2 dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the salts of N-lauroyl, N-myristoyl, or N-palmitoyl sarcosine. The surface active agent is generally present in the potassium salt dentifrice compositions of the present invention at a concentration of about 0.5 to about 5.0% by weight.

Abrasives may be incorporated in the potassium salt dentifrice component of the present invention and preferred abrasives are siliceous materials, such as silica. A preferred silica is a precipitated amorphous hydrated silica, such as Sorbosil AC-35, marketed by Crosfield Chemicals, or Zeodent 115 and Zeodent 165 from Huber Company but other abrasives may also be employed, including sodium metaphosphate, potassium metaphosphate, tricalcium phosphate, calcium phosphate dihydrate, anhydrous dicalcium phosphate, calcium pyrophosphate, magnesium orthophosphate, trimagnesium phosphate, calcium carbonate, sodium bicarbonate, alumina trihydrate, aluminum silicate, zirconium silicate, calcined alumina and bentonite. The concentration of abrasive in the potassium salt desensitizing dentifrice component composition of the present invention will normally be in the range of 2 to about 40% by weight and preferably 5 to 20% by weight.

Other ingredients which may be incorporated in the potassium salt desensitizing component of the present invention, include pigment, sweetener, flavor and preservative. In white dental cream formulations, the pigment of choice is titanium dioxide, rutile, and the proportion thereof will normally be in the range of 0.5 to 1% by weight, preferably 0.75 to 1.25% by weight. The sweetener content will normally be that of an artificial or synthetic sweetener and the normal proportion thereof present will be in the range of 0.1 to 1% by weight, preferably 0.3 to 0.5% by weight. The flavor content, which is preferably of a mixed peppermint/menthol flavor, will usually be in the range of 0.5 to 2% by weight, preferably 0.5 to 1.5% by weight. F.D. & C Grade dyes may be used in appropriate amounts to provide desired colors. The contents of other components or adjuvants of the potassium salt containing dentifrice will normally not exceed 10% by weight, often will be less than 5% by weight, and can be as low as 0%.

To prepare the desensitizing potassium salt dentifrice component of the present invention, the humectant and gelling agent are dispersed in a conventional mixer until the mixture becomes a slurry which is smooth in appearance, after which water is added. This mixture may be heated to 100°–110° F. and mixed for 10 to 30 minutes producing a homogeneous gel phase. The potassium salt is added and mixed for 20 minutes or until completely dissolved. Sweetener and color are added and mixed for 20 minutes. The mixture is transferred to a vacuum mixer. The abrasive is then added and mixed for 10 to 30 minutes at high speed under a vacuum in the range of 5 to 100 millimeter of mercury pressure, preferably 5 to 50 mm Hg, providing a homogenous mixture. The surfactant and oxyethylated hydrogenated castor oil and flavor are then added to the paste which is followed by mixing another 10 to 20 minutes under vacuum of 5 to 50 mm Hg. The resultant product is a stable desensitizing dentifrice of a texture like that of normal toothpastes or gels having a pH in the range of 5 to 8, preferably 6.5 to 7.5, e.g., 7, and of satisfactory flavor.

Stannous salt containing dentifrices useful in the practice of the present invention are known to the art. A stannous salt dentifrice especially useful in the practice of the present invention is disclosed in U.S. Pat. No. 5,578,293, the disclosure of which is incorporated herein by reference. U.S. Pat. No. 5,578,293 discloses an aqueous dentifrice containing stabilized stannous compounds, the dentifrice having antiplaque and antitartar efficacy and is comprised of an aqueous vehicle containing about 10 to about 25% by weight water and about 35 to about 50% by weight of a humectant such as glycerin, sorbitol or mixtures thereof, the vehicle having incorporated therein about 0.05 to about 2% by weight of water soluble stannous ion releasing compound such as stannous fluoride and stannous chloride and mixtures thereof, about 10 to about 40% by weight of a silica abrasive and a combination of about 0.05 to about 2.0% by weight of a water soluble alkali metal pyrophosphate salt such as tetrasodium pyrophosphate and an amount of about 0.01 to about 10% by weight of a polycarboxylic food grade organic acid such as citric acid, sodium citrate or mixtures thereof such amount being sufficient to effectively stabilize the stannous ion, the stabilized stannous ion being present in the composition in an amount effective for therapeutic antiplaque efficacy and the pyrophosphate salt being present in the composition in an amount effective for antitartar efficacy.

The stannous salt containing dentifrice is prepared by first adding the stannous salts mixed with a portion of the water or humectant such as glycerin, sorbitol or mixtures thereof to be used in the preparation of the dentifrice which may be heated to facilitate dissolution to prepare a premix. The premix is then dispersed in the remaining water, humectant, along with thickener, such as xanthan, carboxymethylcellulose and mixtures thereof, sweetener, such as sodium saccharin, organic acid compound, such as citric acid, pyrophosphate salt abrasive, such as silica abrasive, dye or pigment in a conventional mixer until a slurry forms which is smooth in appearance. The mixture is heated to 100°–120° F. for 10–30 minutes to produce a homogeneous gel phase. The gel phase is transferred to a vacuum mixer and the abrasive material is added and mixed for 10–30 minutes at high speed under vacuum in the range of 5 to 100 millimeter of mercury pressure, (mm Hg) preferably 5 to 50 mm Hg to provide a homogenous paste. A surfactant such as sodium lauryl sulfate, the oxyethylated hydrogenated castor oil and flavor are then added to the paste which is followed by mixing another 5 to 10 minutes under vacuum of 5 to 50 mm Hg. The resultant product is a stable dentifrice having a toothpaste or gel texture having a pH in the range of 3 to 7, preferably 5.0 to 6.5, and of satisfactory flavor.

Any convenient means for effecting the separation of the potassium salt from the stannous salt such that the two components are not in direct contact with one another but are nonetheless dispensable from a single packing means. For example, a single container can be compartmentalized so that a SnF$_2$ containing dentifrice component and a potassium salt containing component are housed in separate compartments and are not admixed until applied to the teeth. Such dual compartmented containers are known to the art for example, U.S. Pat. Nos. 4,211,341, 4,687,663, 5,085,853, 5,186,926 disclose dual compartmented tubes and pump means for simultaneous dispensing of dentifrice components containing reactive ingredients.

The following examples are further illustrative of the present invention, but it is understood that the invention is not limited thereto. All amounts and properties referred to herein and the appended claims are by weight.

EXAMPLE

Two sets of dual component dentifrices in which one component contained one or more stannous salts and the second component contained a potassium salt the sets being designated Set I and Set II. Set I and Set II were prepared following the procedures previously described. The vehicle ingredients of the dual component dentifrices of each set were substantially the same except an oxyethylated hydrogenated castor oil prepared by reacting 40 moles of ethylene oxide with hydrogenated castor oil available under the trade designation PEG 40 Castor Oil available from BASF was included in the stannous salt dentifrice component of Set I which was an example of the present invention whereas Set II was a comparative example to which the castor oil compound was not added to either dentifrice component of the set.

The ingredients of the dentifrice components of Set I and II are listed in Tables I and II below. The individual dentifrice components of Set I and II were packaged in separate compartments of a dual compartmented plastic toothpaste tube from which the dentifrice components were dispensed in equal volumes. After 3 months storage at 105° F. inspection of the Set I dual component dentifrice product in which PEG 40 Castor Oil had been incorporated, when dispensed in equal volumes from the dual compartmented tube, indicated that the chemical and cosmetic stability of the stannous salt containing dentifrice component as well the potassium salt dentifrice component was unaffected and was comparable to that of the dispensed comparative Set II dual component dentifrice to which the PEG 40 Castor Oil compound had not been added.

The astringency and palatability of dual component dentifrices Set I and II was evaluated by a monadic, blinded panel test where 70 subjects were asked to brush with either the Set I or Set II dentifrice and rate the product for attributes such as astringency and taste acceptability.

The results of the evaluation tests are recorded in Table III below. In this evaluation test, the lower the mean attribute rating for the dual component dentifrice, the less astringency, sourness and bitterness is noted.

TABLE I

Composition of Dual Component Dentifrice

| Ingredient | Stannous Salt Containing Component (Wt. %) | Potassium Nitrate Containing Component (Wt. %) |
|---|---|---|
| Set I | | |
| Deionized Water | 19.600 | 46.950 |
| Anhydrous Citric Acid | 0.531 | — |
| Sodium Citrate | 2.657 | — |
| Stannous Chloride | 0.600 | — |
| Stannous Fluoride | 0.908 | — |
| PEG 600 | — | 3.00 |
| Potassium Nitrate | — | 10.00 |
| Glycerin | 24.240 | 11.00 |
| Xanthan | 0.400 | 0.800 |
| CMC | 0.300 | 0.250 |
| Sorbitol (70%) | 19.064 | — |
| Sodium Saccharin | 0.400 | 0.400 |
| TSPP | 0.500 | — |
| Titanium Dioxide | — | 0.200 |
| FD&C Blue #1 (1% soln.) | 0.090 | — |
| D&C Yellow #10 (1% soln.) | 0.110 | — |
| PEG 40 Castor Oil | 6.000 | 6.000 |
| Zeodent 115 | 20.000 | 22.000 |
| Zeodent 165 | 2.200 | 3.000 |
| Flavor | 0.900 | 0.900 |
| Sodium Lauryl Sulfate | 1.500 | 1.500 |
| Totals | 100.000 | 100.000 |
| Set II | | |
| Deionized Water | 19.600 | 46.950 |
| Anhydrous Citric Acid | 0.531 | — |
| Sodium Citrate | 2.657 | — |
| Stannous Chloride | 0.600 | — |
| Stannous Fluoride | 0.908 | — |
| PEG 600 | — | 3.00 |
| Potassium Nitrate | — | 10.00 |
| Glycerin | 24.240 | 11.00 |
| Xanthan | 0.300 | 0.800 |
| CMC 12m31p | 0.300 | 0.250 |
| Sorbitol NC 70% | 25.564 | — |
| Sodium Saccharin | 0.400 | 0.400 |
| TSPP | 0.500 | — |
| Titanium Dioxide | — | 0.200 |
| FD&C Blue #1 (1% soln.) | 0.090 | — |
| D&C Yellow #10 (1% soln.) | 0.110 | — |
| Zeodent 115 | 20.000 | 22.000 |
| Zeodent 165 | 1.8000 | 3.000 |
| Flavor | 0.900 | 0.900 |
| Sodium Lauryl Sulfate | 1.500 | 1.500 |
| Totals | 100.000 | 100.000 |

TABLE III

Dual Component Dentifrice

| | Set I | Set II |
|---|---|---|
| Taste Attribute | | |
| Astringency* | 3.2$^b$ | 4.6$^a$ |
| Sourness* | 3.9$^a$ | 4.1$^a$ |
| Bitterness* | 3.6$^a$ | 4.0$^a$ |

*Panelist rating of intensity.

*Scale: 1 = not at all, 3 = slightly, 5 = moderately, 7 = very, 9 = extremely Recorded data with different superscript letters are significantly different at a 90% confidence level whereas the same superscript letters are not statistically significantly different but indicate trends.

The results recorded in Table III indicate that astringency which is normally prevalent in stannous fluoride dentifrices was significantly reduced by the combined presence in the dual component dentifrice of 6% by weight of the hydrogenated castor oil.

For purposes of further comparison, the procedure of the Example was repeated with the exception that the amount of hydrogenated castor oil in the combined dentifrice components was varied from 2-4% by weight. The results of the astringency and palatability panelist evaluation is recorded in Table IV below.

TABLE IV

| Stannous Salt Dentifrice Component (Wt. %) Hydrogenated Castor Oil | Potassium Nitrate Containing Dentifrice Component (Wt. %) Hydrogenated Castor Oil | Ast. | Sour | Bitter |
| --- | --- | --- | --- | --- |
| 4% | — | 3.47 | 3.51 | 3.55 |
| 4% | 4% | 3.22 | 3.51 | 3.33 |
| 6% | — | 3.45 | 3.58 | 3.42 |
| 6% | 6% | 3.20 | 3.27 | 3.44 |
| — | — | 3.87 | 3.53 | 3.71 |

The results recorded in Table IV indicate that when the combined presence of the hydrogenated castor oil in the dual component dentifrice is less than 6%, that is 2-4% by weight optimal reduction of astringency is not achieved.

What is claimed is:

1. A two component desensitizing dentifrice composition wherein the components are separated from one another but are nonetheless dispensable from a single packaging means, the composition being comprised of a first dentifrice component containing a desensitizing potassium salt and a second dentifrice component containing a stannous salt desensitizing agent and free of potassium salt, the first dentifrice component being free of stannous salt wherein at least one component has incorporated therein the reaction product of the oxyethylation of hydrogenated castor oil so that the components when dispensed and combined for use, contain at least about 6% by weight of the composition whereby less astringency is experienced by the user of the composition.

2. The composition of claim 1 wherein the potassium salt is potassium nitrate.

3. The composition of claim 1 wherein the stannous salt is stannous fluoride.

4. The composition of claim 1 wherein the oxyethylated hydrogenated castor oil is the reaction product of ethylene oxide and hydrogenated castor oil.

5. The composition of claim 1 wherein the oxyethylated hydrogenated castor oil is present in a dentifrice component at a concentration of about 6 to about 8% by weight.

6. A method for treating dentin hypersensitivity while limiting astringency during use which comprises preparing a first dentifrice component containing a desensitizing potassium salt and a second dentifrice component containing a stannous salt, and free of potassium salt the first dentifrice component being free of stannous salt incorporating in at least one dentifrice component a compound which is the reaction product of the oxyethylation of hydrogenated castor oil, maintaining the first and second dentifrice components separate from the other until dispensed for application to teeth requiring relief from dentine hypersensitivity and then combining the separate dentifrice components and applying the combined components to the teeth, the combined composition containing at least about 6% by weight of the oxylated castor oil.

7. The method of claim 6 wherein the potassium salt is potassium nitrate.

8. The method of claim 6 wherein the stannous salt is stannous fluoride.

9. The method of claim 6 wherein the oxyethylated hydrogenated castor oil is the reaction product of ethylene oxide and hydrogenated castor oil.

10. The method of claim 6 wherein the oxyethylated hydrogenated castor oil is present in a dentifrice component at a concentration of about 6 to about 8% by weight.

* * * * *